United States Patent [19]

Kappner et al.

[11] Patent Number: 4,622,297

[45] Date of Patent: Nov. 11, 1986

[54] PROCESS AND AGENT FOR TESTING THE SENSITIVITY OF BACTERIA

[75] Inventors: Manfred Kappner, Reinheim; Harald Metz, Bickenbach, both of Fed. Rep. of Germany

[73] Assignee: Merck Patent Gesellschaft mit beschränkter Haftung, Darmstadt, Fed. Rep. of Germany

[21] Appl. No.: 637,192

[22] Filed: Aug. 2, 1984

[30] Foreign Application Priority Data

Aug. 2, 1983 [DE] Fed. Rep. of Germany ....... 3327839

[51] Int. Cl.[4] .................. C12Q 1/18; C12Q 1/34; C12Q 1/26; C12Q 1/20
[52] U.S. Cl. ........................ 435/32; 435/18; 435/25; 435/33; 435/810
[58] Field of Search .............. 435/18, 25, 32, 33, 435/810

[56] References Cited

U.S. PATENT DOCUMENTS 3,197,384 7/1965 Goldman .............................. 435/33
3,506,544 4/1970 Silverman et al. ................ 435/25 X
3,509,026 4/1970 Sanders ............................ 435/25 X
4,242,446 12/1980 Madappally et al. ................ 435/15

FOREIGN PATENT DOCUMENTS 2026693 2/1980 United Kingdom ................. 435/32

OTHER PUBLICATIONS

T. J. Franklin & G. A. Snow, "The Bacterial Cell Wall—A Vulnerable Shield", *Biochemistry of Antimicrobial Action*, Chapman & Hall, London, 1971, pp. 22–55.
H. U. Bergmeyer, *Methoden der Enzymatischen Analyse*, Verlag Chemie Weinheim/Bergstr., 1974, 129–139.
*The Prokaryotes*, vol. 1, Starr et al. (eds.), 1981, Springer-Verlag, Berlin, p. 19.
*Microbiology*, 2nd Ed., David et al., 1983, Harper and Row, MD, pp. 123–124.

Primary Examiner—Robert J. Warden
Assistant Examiner—Patricia Kate White
Attorney, Agent, or Firm—Millen & White

[57] ABSTRACT

A process and agent are provided for testing the sensitivity of bacteria towards antibiotics with a primary action in murein biosynthesis. The process is characterized in that the cytoplasmic enzyme activities released from the bacteria in the presence of the antibiotic and an enzyme substrate are determined directly.

23 Claims, No Drawings

PROCESS AND AGENT FOR TESTING THE SENSITIVITY OF BACTERIA

BACKGROUND OF THE INVENTION

The invention relates to a process and agent for testing the sensitivity of bacteria towards antibiotics with a primary action in murein biosynthesis.

Before antibiotic therapy, the sensitivity of the pathogen towards various antibiotics should, where possible, be determined. The test methods used today for testing the sensitivity are mostly based on detection of the inhibition of growth of pure cultures of the microorganism in the presence of the antibiotic.

In an in vitro sensitivity test, the antibiotic action depends on many factors, for example on the growth phase of the microorganisms, the nutrient medium and the polulation density. Standard methods for testing the sensitivity of microorganisms towards antibiotics are the dilution test in agar or a broth and the agar diffusion test.

The tests are in practice evaluated by visual examination of the test batches with respect to microorganism growth, for example after 24 hours incubation, by determination of the turbidity in the dilution series test or of the inhbiting areola diameter in the agar diffusion test. The analysis times in the dilution series test can usually be shortened to 4–8 hours by modern sensitive analytical methods, such as impedance measurement or laser nephelometry. However, the corresponding analytical instruments are as a rule expensive, so that their use is only justified in laboratories with a large number of samples; with average analytical times of 4–8 hours, the result is frequently available only after office hours, so that the advantage of the shortened analytical time is cancelled out again by the delayed forwarding of information.

In practice, there is therefore an urgent need for a sensitivity test which gives results very rapidly and can also be carried out in smaller laboratories without too great an expenditure on apparatus. Rapid tests to ascertain the sensitivity of microorganisms towards chemotherapeutics makes more controlled use of the antibiotics possible, which leads, for example, to a shortening in the treatment time for the patient and to a check in the selectioning of multi-resistant bacterial strains.

The antibiotics whose primary site of action is murein biosynthesis include, for example, cycloserine, vancomycin and bacitracin, in addition to the penicillins and cephalosporins, which are very useful in therapy. Penicillins and cephalosporins are characterized chemically by the presence of a β-lactam ring. The resistance properties of Gram-negative bacteria towards β-lactam antibiotics is different from that of Gram-positive organisms. Most of the Gram-positive bacteria produce relatively large amounts of extracellular β-lactamases which split the β-lactam ring and can thus inactivate the β-lactam antibiotics. For the sensitivity of Gram-negative bacteria towards β-lactam antibiotics, a penetration resistance is frequently of substantially greater importance than a resistance caused by β-lactamases. The cell-linked β-lactamases from Gram-negative bacteria are formed in substantially lower concentrations than the extracellular β-lactamases from Gram-positive bacteria. In the case of Gram-negative bacteria, there is frequently no correlation between the minimum inhibitory concentration of the β-lactam antibiotics and the β-lactamase activity. β-Lactamase-positive bacteria are to be found among both the β-lactam antibioticsensitive and the β-lactam antibiotic-insensitive Gram-negative bacteria. The known rapid β-lactamase tests thus are of no significance by themselves for testing the sensitivity of, for example, Enterobacterianceae towards β-lactam antibiotics.

SUMMARY OF THE INVENTION

Accordingly, it is an object of this invention to provide a simple process and a rapid test system for testing the sensitivity of bacteria towards antibiotics with a primary site of action in murein biosynthesis, e.g., with analytical times significantly below 4 hours.

Upon further study of the specification and appended claims, further objects and advantages of this invention will become apparent to those skilled in the art.

These objects have been achieved providing a process for testing the sensitivity of bacteria towards antibiotics with a primary action in murein biosynthesis, comprising directly determining the cytoplasmic enzyme activities released from the bacteria in the presence of the antibiotic and an enzyme substrate.

The invention furthermore relates to an agent for testing the sensitivity of bacteria towards antibiotics with a primary action in murein biosynthesis, which essentially contains a buffered nutrient medium with various antibiotic concentrations, at least one enzyme substrate and, if appropriate, at least one coenzyme and, if appropriate, at least one redox indicator.

DETAILED DISCUSSION

The process and agent according to the invention make it possible, by simple and rapid measurement of the activity of cytoplasmic enzymes, to ascertain the influence of antibiotics on murein biosynthesis directly within a single generation cycle of the bacterium, for example by carrying out a test on the sensitivity of bacteria towards β-lactam antibiotics within 30–60 minutes. A sensitivity of the bacterium towards the antibiotic can be detected more rapidly by the process according to the invention than by known processes in which the growth rate of the bacteria in the presence of the antibiotic is usually monitored. In these processes, incubation times corresponding to several generation cycles of the bacterium are necessary.

In the process according to the invention, a single bacteria colony about 1 mm in size from a solid nutrient medium is sufficient as the inoculum for carrying out the sensitivity test. The principle of the test, according to the invention, to ascertain the sensitivity of bacteria towards antibiotics, is direct detection of damage to growing bacteria in the presence of an antibiotic with a primary site of action in murein biosynthesis. When the murein biosynthesis is interfered with, an imcomplete, that is to say a fragmented, murein skeleton results. If the murein skeleton cannot offer the appropriate counterpressure to the osmotic pressure of the bacteria in a hyptonic medium, the cells burst and intracellular enzymes are released. The cytoplasmic enzyme activities released in the presence of various antibiotic concentrations are a reliable measure of the sensitivity of the bacteria towards the antibiotic. Bursting of the cells in the case of an only slightly damaged murein skeleton can be promoted by a small concentration of detergent. Usually, no cytoplasmic enzyme activities or only very low cytoplasmic enzyme activities are to be detected under the chosen test conditions below the so-called minimum inhibitory concentration of the antibiotic. At antibiotic concentrations equal to or greater than the minimum inhibitory concentration, substantial cytoplasmic enzyme activities are detectable which, for example, correspond to the cytoplasmic enzyme activities which can be releaseed by ultrasonic treatment of the cells.

The cytoplasmic enzymes which are used for testing the sensitivity of bacteria towards β-lactam antibiotics can be enzymes which occur ubiquitously in bacteria, e.g. enzymes of the catabolic glucose pathway, or enzymes of the oxidative phosphorylation in aerobic bacteria. If the bacterial family, genus, species or even strain is known, it is also possible and generally preferred to utilize cytoplasmic enzymes which are specific thereto, providing significant advantages.

In the case of Gram-negative bacteria of medical interest, which have been isolated on MacConkey agar as a selective nutrient medium, a positive β-galactosidase activity, for example, indicates the existence of a representative of the genera Escherichia, Citrobacter, Klebsiella, Enterobacter, Hafnia, Serratia or Arizona. In the inventigation of cytoplasmic enzyme activity specific for one species of bacteria, the sensitivity of the corresponding species of bacteria can be tested even in a mixed culture containing other species of bacteria. There is thus no delay in carrying out a sensitivity test on the probable pathogen caused by the need to isolate pure cultures. For example, in contrast to other coliform germs, Escherichia coli usually displays a powerful cytoplasmic β-D-glucuronidase activity. The sensitivity of Escherichia coli towards β-lactam antibiotics can thus be determined simply and rapidly in a mixed culture of various coliform bacteria by determining the presence of this enzyme.

The test system usually has the follwing compositon: buffered nutrient media with various antibiotic concentrations, one or more enzyme substrates, preferably fluorogenic or chromogenic substrates, and, if appropriate, one or more coenzymes (cofactors), and, if appropriate, at least one redox indicator. The test system preferably also contains a detergent. To test the sensitivity of bacteria towards antibiotics, the test system is inoculated with a suspension of the bacterium to be investigated.

Buffered nutrient media which can be used are fully conventional for example, Müeller-Hinton broth, brain-heart broth and casein peptone-soya meal peptone broth in suitable buffers, such as phosphate buffer, tris(hydroxymethyl)-aminomethane (tris buffer), N-(2-hydroxethyl)-piperazine-N-2-ethanesulfonic acid (HEPES buffer) or other customary buffer systems. A preferred buffer is a 0.1 M phosphate buffer of pH value 7. The choice of buffer and of the pH value depends both on the optimum test conditions of the enzyme to be detected and also on the suitable physiological conditions for the bacteria. The expert can determine the suitable conditions by routine methods. Unless indicated otherwise herein, all details of the test conditions and procedures for the enzymatic determinations can be routinely determined and optimized using conventional considerations and techniques, e.g., as discussed in H. U. Bermeyer, Methoden der enzymatischen Analyse, Verlag Chemie, Weinheim/Bergstr., 3rd Ed., 1974, which disclosure is incorporated by reference herein.

Examples of antibiotics with a primary site of action in murein biosynthesis include penicillins, e.g., penicillin G, penicillin V and ampicillin, cephalosporins, such as cephalosporin C, cephaloridine, cephalothin, vancomycin, cycloserine and bacitracin. See, T. J. Franklin, G. A. Snow, Biochemistry of Antimicrobial Action, Chapman and Hall Ltd., London, 1971, which disclosure is incorporated by reference herein, for other antibiotics with the appropriate properties. The final concentrations of the antibiotics in the incubation batch should increase in a range of from 0 to 64 μg/ml, preferably in a range up to 8 μg/ml. Precise values for a given system will be optimized by routine preliminary tests in view of the antibiotics minimum inhibitory concentration.

In practice, it is also possible to carry out the method of this invention utilizing fewer incubation samples, even only a single sample containing an amount of an antibiotic known to be greater than its minimum inhibitory samples could be used, one containing such an amount of antibiotic and one containing no antibiotic.

The cytoplasmic enzyme activities released from the bacteria in the presence of the antibiotic which can be most easily detected are preferably hydrolytic enzymes (hydrolases), for example glycosidases, such as β-D-galactosidase and β-D-glucuronidase, or oxidoreductases, such as succinate dehydrogenase and malate dehydrogenase.

The enzyme activities of glycosidases can be determined, for example, with the aid of fluorogenic or chromogenic substrates. Such substrates are, for example, for β-D-galactosidase: α- or β-naphthyl β-D-galactopyranoside, o- or p-nitrophenyl β-D-galactopyranoside and 4-methyl-umbelliferyl β-D-galactopyranoside; for β-D-glucuronidase: α- or β-naphthyl β-D-glucuronide, o-or p-nitrophenyl β-D-glucuronide and 4-methylumbelliferyl β-D-glucuronide. The cytoplasmic enzyme activities of the oxidoreductases can be determined in the customary manner with the aid of the corresponding enzyme substrates and coenzymes, it also being possible for fluorogenic or chromogenic redox reactions subsequently to take place. Examples of suitable coenzymes are NAD, NADP and the reduced forms NADH and NADPH. Suitable redox indicators are those of which the oxidized and reduced form can be unambiguously differentiated visually, photometrically or by electrochemical methods, for example tetrazolium salts, such as 3-(4-iodophenyl)-2-(4-nitrophenyl-5-phenyl-2H-tetrazolium chloride and 3-(4,5-dimethyl-thiazol-2-yl)-2,5-diphenyl-2H-tetrazolium bromide. Depending on the type of the redox initiators, the transfer of electrons can be effected directly or with the aid of a so-called electron transfer agent. Examples of possible electron transfer agents include phenazine methosulfate, phenazine ethosulfate, meldola blue and diaphorase.

In general, any system compatible substrate for the enzyme of interest can be used as long as it provides a means for recognizing the presence of the enzyme.

The substrates and test conditions suitable for the particular enzyme are known from the literature or can be determined by standard methods. The enzyme substrates are usually employed in concentrations of $10^{-1}$ to $10^{-5}$ M.

The bacteria to be tested for sensitivity towards antibiotics can be used, for example, as pure cultures which have been obtained from blood agar, casein peptone-soya meal peptone agar, brolacin agar or similar nutrient media. The bacterial suspension in the test batch should usually have a germ count of $10^5$–$10^8$ germs/ml.

The agent according to this invention preferably contains cationic, anionic and/or non-ionic detergents.

These are not critical in respect of their type, and they can be selected from the detergents usually employed to burst cells. Polyoxyethylene derivatives of sorbitan esters, such as polyoxyethylene sorbitan monolaurate, polyoxyethylene sorbitan monopalmitate and polyoxyethylene sorbitan monooleate, for example, have proved suitable. These are used in concentrations of $10^{-4}$ to $10^{-6}$ M; at these detergent concentrations, no significant amounts of cytoplasmic enzymes are released from cells with an intact murein skeleton.

In general, any property of the nutrient medium can be adjusted to provide the necessary incubation system as long as it only affects the ability of bacterial cells having disrupted murein components to survive. For example, any of the usual conditions adjusted to cause cells to lyse can be employed in conjunction with this invention as long as the resultant conditions are effective to burst cells which have a disrupted murein component, but not to burst cells which have a normal murein component.

The test system preferably comprises a deepdrawn component with numerous cavities, about 100 $\mu$l in size, a commercially available microtiter plate or a particular cell rail; the reagents of the test system are advantageously in lyophilized form.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

A colony, about 1 mm in size, of a culture 12–18 hours old (overnight culture) of Enterobacter cloacae on brolacin agar is suspended in 1.0 ml of 0.1 M phosphate buffer, pH 7.0. In each case 100 $\mu$l of the bacterial suspension is added to 100 $\mu$l of test solution of various concentrations of ampicillin (D-(−)-α-aminobenzylpenicillin) in the cavities of a microtiter plate. The final concentrations of ampicllin in the incubation batch are 0–0.5–1.0–2.0–4.0–8.0 $\mu$g/ml.

The test solution consists of twice-concentrated Muller-Hinton broth in 0.1 M phosphate buffer, pH 7.0, which is $2\times10^{-5}$ M in 4-methylumbelliferyl β-D-galactopyranoside and $2\times10^{-5}$ M in octylphenol polyetylene glycol ether and which contains the abovementioned ampicillin concentrations. After incubation of the test batch at 37° C. for 30 minutes, the microtiter plate is irradiated with a UV lamp at 366 nm. Inhibition of murein biosynthesis by ampicillin is to be recognized in fluorescence of the test batch as a result of significant β-D-galactosidase activity in comparison with the control without the antibiotic or batches with antibiotic concentrations below the minimum inhibitory concentration. The test batches containing 4.0 and 8.0 $\mu$g/ml of ampicillin exhibit significant fluorescence, that is to say murein biosynthesis of Enterobacter cloacae is inhibited under the chosen test conditions at these ampicillin concentrations.

EXAMPLE 2

A bacterial suspension containing about $10^7$ germs/ml in 0.1 M phosphate buffer, pH 7.0, is prepared from an overnight culture of Escherichai coli on blood agar. In each case 100 $\mu$l of the bacterial suspension is added to 100 $\mu$l of test solution, containing various cycloserine concentrations, in the cavities of a microtitre plate. The end concentration of cycloserine in the test batch is 0–0.5–1.0–2.0–4.0–8.0 $\mu$g/ml.

The test solution is a twice-concentrated MullerHinton broth in 0.1 M phosphate buffer, pH 7.0, which is $2\times10^{-5}$ M in 4-methylumbelliferyl β-D-glucuronide and $2\times10^{-5}$ M in octylphenol polyethylene glycol ether and contains the abovementioned cycloserine concentrations.

After incubation of the test batch at 37° C. for 30 minutes, the microtiter plate is irradiated with a UV lamp at 366 nm. The test batches containing 4.0 and 8.0 $\mu$g/ml of cycloserine exhibit a significant fluorescence as a result of significant β-D-glucuronidase activity, that is to say the minimum inhibitory concentration of cycloserine in the case of Escherichia coli is 4.0 $\mu$g/ml under the chosen test conditions.

EXAMPLE 3

10 colonies, about 1 mm in size, of a culture 16–20 hours old of Citrobacter freundii on blood agar are suspended in 5 ml of 0.1 M phosphate buffer, pH 7.4. In each case 0.5 ml of the bacterial suspension is added to 0.5 ml of test solution containing various concentrations of ampicillin. The end concentrations of ampicillin in the incubation batch are 0–0.5–1.0–2.0–4.0–8.0–16.0 $\mu$g/ml.

The test solution consists of twice-concentrated Muller-Hinton broth in 0.1 M phosphate buffer, pH 7.4, which is $2.10^{-3}$ M in oxaloacetate, $4.10^{-4}$ M in NADH and $2.10^{-5}$ M in octylphenol polyethylene glycol ether. After incubation of the test batch at 37° C. for 45 minutes, the malate dehydrogenase activity is measured by determining the NADH content (extinction measurement at 340 nm).

Inhibition of murein biosynthesis by ampicillin is to be recognized in a significantly lower extinction of the test batch at 340 nm in comparison with the control without the antibiotic or batches with antibiotic concentrations below the minimum inhibitory concentration. The test batches containing 8.0 and 16.0 $\mu$g/ml of ampicillin exhibit a significantly lower extinction at 340 nm, that is to say a significant malate dehydrogenase activity can be detected in these test batches. Under the chosen test conditions, murein biosynthesis in Citrobacter freundii is inhibited at 8.0 and 16.0 $\mu$g/ml of ampicillin.

EXAMPLE 4

A kit for testing the sensitivity of a bacterium towards an antibiotic which acts primarily by disrupting murein biosynthesis comprises a deep drawn component with 6 cavities of about 100 $\mu$l in size. The cavities contain in lyophilized form an antibiotic free control and 5 different antibiotic concentrations in a buffered nutrient medium together with the fluorogenic or chromogenic enzyme substrate and a detergent.

What is claimed is:

1. A method for testing the sensitivity of a bacterium toward an antibiotic which acts primarily by distrupting murein biosynthesis in growing bacteria, comprising, culturing the bacterium in a nutrient medium therefor which also contains an amount of the antibiotic equal to or greater than its minimum inhibitory concentration for the bacterium, and a substrate for a cytoplasmic enzyme of the bacterium, wherein said medium is substantially not effective to burst cells of the bacterium having a normal murein component, but is effective to burst bacterial cells having an abnormal murein component, and determining the presence of a substantial amount of the cytoplasmic enzyme by observing a property of the resultant medium which is sensitive to the interaction of the enzyme with its substrate, whereby the presence of a substantial amount of the cytoplasmic enzyme indicates the sensitivity of the bacterium toward the antibiotic.

2. A method of claim 1 wherein the cytoplasmic enzyme is one which is essentially ubiquitous in bacteria.

3. A method of claim 1 wherein the cytoplasmic enzyme is specific for the genus of bacteria being tested.

4. A method of claim 1 wherein the cytoplasmic enzyme is specific for the species of the bacteria being tested.

5. A method of claim 1 wherein the cytoplasmic enzyme is a hydrolytic enzyme.

6. A method of claim 5 wherein the hydrolytic enzyme substrate is a fluorogenic or chromogenic enzyme substrate.

7. A method of claim 1 wherein the cytoplasmic enzyme is an oxidoreductase.

8. A method of claim 7 wherein the medium further comprises a coenzyme for the oxidoreductase or a fluorogenic or chromogenic redox indicator.

9. A method claim 1 wherein the determination is conducted within 60 minutes of the onset of the culturing.

10. A method of claim 1 wherein the nutrient medium comprises a compatible buffer.

11. A method of claim 1 wherein the nutrient medium further comprises an amount of a detergent effective to burst cells of the bacterium which have an abnormal murein component but essentially ineffective to burst cells having a normal murein component.

12. A method of claim 11 wherein, in the medium, the concentration of the antibiotic is up to 64 $\mu$g/ml, of the substrate is $10^{-1}$ to $10^{-5}$M, of the bacteria is $10^5$ to $10^8$ germs/ml and of the detergent is $10^{-4}$ to $10^{-6}$M.

13. A method of claim 1 wherein the antibiotic has a $\beta$-lactam structure.

14. A method claim 1 wherein the antibiotic is a penicillin or a cephalosporin.

15. A method of claim 1 wherein the culturing of the bacterium is further conducted separately in individual samples of the nutrient medium containing different concentrations of the antibiotic.

16. A method of claim 15 wherein the culturing is also simultaneously conducted in a nutrient medium containing no antibiotic or containing less than its minimum inhibitory concentration.

17. A method of claim 1 wherein the enzyme is a glycosidase.

18. A method of claim 1 wherein the observation of the enzyme-substrate interaction is conducted visually, photometrically or electrochemically.

19. A kit for testing the sensitivity of a bacterium towards an antibiotic which acts primarily by disrupting murein biosynthesis, comprising separate containers, each containing a sample of buffered nutrient medium for the bacterium and each containing a different concentration of the antibiotic, a substrate for a cytoplasmic enzyme of the bacterium, and an amount of a detergent effective to burst cells of the bacterium which have an abnormal murein component but essentially ineffective to burst cells having a normal murein component, wherein at least one concentration of the antibiotic is equal to or greater than its minimum inhibitory concentration for the bacterium.

20. A kit of claim 19 wherein the nutrient media further comprise a coenzyme for the cytoplasmic enzyme or a redox indicator.

21. A kit of claim 19 wherein the antibiotic has a $\beta$-lactam structure.

22. A kit of claim 19 wherein the concentrations of the antibiotic are up to 64 g/ml, of the substrate are $10^{-1}$ to $10^{-5}$ M, and of the detergent are $10^{-4}$ to $10^{-6}$ M.

23. A method of claim 1, wherein the cytoplasmic enzyme is one in the catabolic glucose pathway or one functioning in oxidative phosphorylation in aerobic bacteria.

* * * * *